United States Patent

Seko et al.

[11] Patent Number: 6,037,509
[45] Date of Patent: Mar. 14, 2000

[54] PROCESS FOR PRODUCING 1-BROMO-4-PHENYLBUTANE

[75] Inventors: Shinzo Seko, Toyonaka; Atsushi Furutani, Takatsuki, both of Japan

[73] Assignee: Sumitomo Chemical Company, Limited, Osaka, Japan

[21] Appl. No.: 09/289,385

[22] Filed: Apr. 12, 1999

[30] Foreign Application Priority Data

Apr. 10, 1998 [JP] Japan .................................. 10-099614

[51] Int. Cl.$^7$ .................................................. C07C 22/00
[52] U.S. Cl. .......................................................... 570/195
[58] Field of Search ............................................. 570/195

[56] References Cited

U.S. PATENT DOCUMENTS 4,051,190  9/1977  Dunnigan .
4,432,971  2/1984  Karanewsky et al. .
5,637,736  6/1997  Fujishima et al. .

FOREIGN PATENT DOCUMENTS 3-95144   4/1991   Japan .
6-345675  12/1994  Japan .

OTHER PUBLICATIONS

Z. Niu et al., "Synthesis of 4–phenyl–1–butanol", *Huaxue Shiji*, vol. 17, No. 5, (1995), pp. 317 and 288, month not available.

L. R. Sousa et al., "Halopolycarbon Homologation", *Journal of the American Chemical Society*, vol. 96, No. 22, Oct. 1974, pp. 7101–7103.

S. H. Wilen et al., "35—Noncondensed Aromatic Compounds", *Chemical Abstracts*, vol. 58, (1963), 11242, month not available.

*Primary Examiner*—Alan Siegel
*Attorney, Agent, or Firm*—Sughrue, Mion, Zinn, Macpeak & Seas, PLLC

[57] ABSTRACT

A process for producing 1-bromo-4-phenylbutane of the formula (1):

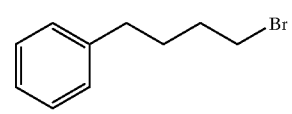

(1)

which is characterized by the steps of;
reacting 4-bromobutyryl halide of the formula (2):

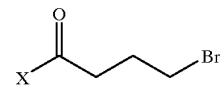

(2)

where X is a halogen atom, with benzene in the presence of a Lewis acid to give a 4-bromobutyrophenone of the formula (3):

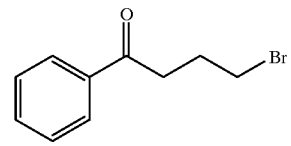

(3)

and reacting 4-bromobutyrophenone compound of the formula (3) with hydrogen in the presence of a metal catalyst.

5 Claims, No Drawings

PROCESS FOR PRODUCING 1-BROMO-4-PHENYLBUTANE

BACKGROUND OF THE INVENTION

1. Field of the Invention

The present invention relates to an industrially advantageous process for producing 1-bromo-4-phenylbutane.

2. Description of the Related Art

A known process for producing 1-bromo-4-phenylbutane involves reacting benzene with 4-halobutanol in the presence of a Lewis acid catalyst to give 4-phenylbutanol, followed by bromination (Japanese Laid-open Patent Publication No. 03-95144/1991). However, it is difficult to inhibit dialkylated compounds from being produced as by-products in reacting benzene with 4-halobutanol, since monoalkylated compounds produced have a higher reactivity than benzene.

Further, a process is known in which benzene is reacted with 1-bromo-4-chlorobutane in the presence of a Lewis acid catalyst (Chem. Abstr. 58, 11242g(1963)). However, this process also involves difficulty in inhibiting dialkylated compounds as described before.

SUMMARY OF THE INVENTION

In view of the above, the inventors of the present invention have made an extensive research for a process of producing 1-bromo-4-phenylbutane in a good yield and efficiently from inexpensive materials and completed the present invention.

DESCRIPTION OF THE PREFERRED EMBODIMENTS

The present invention provides: a process for producing 1-bromo-4-phenylbutane of the formula (1):

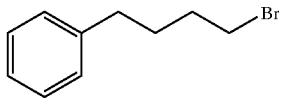

(1)

which comprises the steps of;
reacting 4-bromobutyryl halide of the formula (2):

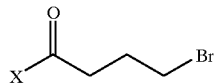

(2)

where X is a halogen atom, with benzene in the presence of a Lewis acid to give a 4-bromobutyrophenone of the formula (3):

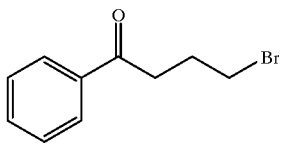

(3)

and
reacting 4-bromobutyrophenone of the formula (3) with hydrogen in the presence of a metal catalyst.

Hereafter, the present invention will be explained in more detail.

In the compounds of the formula (2) of the present invention, the halogen atom for X may be, for example, a chlorine atom, a bromine atom, or an iodine atom.

Examples of the 4-bromobutyryl halide (2) used in the reaction of 4-bromobutyryl halide (2) with a benzene to give 4-bromobutyrophenone (3) include, for example, 4-bromobutyryl chloride, 4-bromobutyryl bromide.

The 4-bromobutyryl halide (2) can be readily obtained, for example, by reacting γ-butyrolactone with hydrogen bromide to give 4-bromobutyric acid, which can be then converted to an acid halide. Also, the acid halide, 4-bromobutyryl halide (2) may be produced from 4-bromobutyric acid in situ prior to the reaction with benzene and used as it is in the reaction of the present invention.

4-Bromobutyric acid may be produced, for example, by a reaction of γ-butyrolactone with hydrogen bromide. The hydrogen bromide to be used may be gas or an aqueous solution thereof. The reaction temperature is usually about 10 to 100° C., and the amount of hydrogen bromide to be used is usually about 1 to 10 moles per mole of γ-butyrolactone.

4-Bromobutyryl halide (2) may be produced by a reaction of 4-bromobutyric acid with a halogenating agent.

The reaction temperature is usually about 0 to 80°C., and examples of the halogenating agent to be used include a conventionally used halogenating agent, for example, thionyl chloride, thionyl bromide, phosphorus pentachloride, phosphorus trichloride, phosphorus pentabromide, phosphorus tribromide, phosgene, diphosgene, or triphosgene.

The amount of the halogenating agent to be used is usually 0.3 to 3 moles per mole of 4-bromobutyric acid.

In the reaction of 4-bromobutyryl halide (2) with benzene in the presence of a Lewis acid to give a 4-bromobutyrophenone (2), benzene is usually used in an amount of 1 to 200 moles per mole of 4-bromobutyryl halide (2) and may be used as a solvent as well.

The Lewis acid to be used in the reaction may be, for example, tin halide, aluminum halide, iron halide, zinc halide, boron halide, titanium halide, or metal trifluoromethanesulfonate. More specifically, the Lewis acid may be, for example, stannous chloride, stannic chloride, stannous bromide, stannic bromide, aluminum chloride, aluminum bromide, ferrous chloride, ferric chloride, zinc chloride, zinc bromide, boron trifluoride, titanium tetrachloride, scandium trifluoromethanesulfonate, ytterbium trifluoromethanesulfonate, lanthanum trifluoromethanesulfonate, samarium trifluoromethanesulfonate, or hafnium trifluoromethanesulfonate, among which aluminum chloride is especially preferable.

The amount of the Lewis acid to be used may be 0.2 to 2 moles, preferably 0.8 to 1.5 moles, per mole of 4-bromobutyryl halide (2).

The reaction is preferably carried out in benzene as a solvent. However, other solvents may be used instead. Examples of the solvent to be used include, for example, a halogenated solvent such as dichloromethane or 1,2-dichloroethane, or a solvent conventionally used in an ordinary Friedel-Crafts reaction, such as carbon disulfide or nitromethane.

The amount of the solvent to be used is usually 1 to 100 parts by weight per 1 part by weight of 4-bromobutyryl halide (2), but is not specifically limited.

The reaction temperature is usually within the range of −50 to 100° C., preferably −20 to 50° C.

The reaction may be carried out, for example, by adding the 4-bromobutyryl halide (2) into a mixture of the benzene and the Lewis acid, or by adding the benzene into a mixture of the Lewis acid and 4-bromobutyryl halide (2) in a solvent, although the method of carrying out the reaction is not specifically limited.

After completion of the reaction, the 4-bromobutyrophenone (3) can be isolated readily by a conventional procedure, for example, washing, extraction, concentration, and/or distillation. The obtained 4-bromobutyrophenone (3) in a solution form may be used in the next step as it is without any further purification.

Subsequently, the 4-bromobutyrophenone (3) as obtained above is reacted with hydrogen in the presence of a metal catalyst to give 1-bromo-4-phenylbutane.

Examples of the metal catalyst to be used in the above reaction include a transition metal catalyst of the Groups 8, 9 and 10 of the Periodic Table such as a palladium, platinum, nickel, ruthenium, rhodium, or iridium catalyst, preferably a palladium, platinum, nickel, or ruthenium metal catalyst.

More specifically, examples of the metal catalyst include, for example, palladium, palladium chloride, palladium oxide, palladium hydroxide, palladium acetate, platinum, platinum oxide, Raney nickel, ruthenium, rhodium, or iridium, which may be supported on activated carbon or may be a complex having a variety of ligands. A mixture of two or more of the metal catalysts may be used as well.

The amount of the metal catalyst to be used is 0.0001 to 0.5 part by weight, preferably 0.001 to 0.1 part by weight per 1 part by weight of 4-bromobutyrophenone (3).

The reaction may be carried out in benzene used as a solvent or with another solvent. Examples of the solvent to be used in the reaction include, for example, an alcohol solvent such as methanol, ethanol, isopropanol, or butanol, an aromatic solvent such as benzene or toluene, an ether solvent such as diethyl ether, tetrahydrofuran, 1,4-dioxane, dimethoxyethane, or t-butyl methyl ether, water, or acetic acid, preferably an alcohol solvent, more preferably methanol, ethanol, or isopropanol. A mixture containing two or more of these solvents may be used as well.

The amount of the solvent to be used is usually 0.5 to 100 parts by weight per 1 part by weight of 4-bromobutyrophenone (3).

The pressure of hydrogen to be used is preferably within the range from ordinary pressure to 10 MPa, but is not specifically limited, depending on the catalyst, the temperature condition, or the like.

The reaction temperature is usually within the range of 0 to 100° C., preferably 10 to 70° C.

After completion of the reaction, the 1-bromo-4-phenylbutane can be readily isolated by a conventional process such as washing, extraction, concentration, or distillation.

According to the production process of the present invention, 1-bromo-4-phenylbutane can be obtained efficiently from inexpensive materials.

EXAMPLES

Hereafter, the present invention will be explained more specifically with reference to the following embodiments, which are not to be construed to limit the scope of the present invention.

Example 1

A suspension solution of 3.9 g of benzene (50 mmol) and 1.33 g of aluminum chloride (10 mmol) was cooled to 10°C., and 1.95 g of 4-bromobutyryl chloride (purity: 95%, 10 mmol) was dropwise added to the above solution at the same temperature. After raising the temperature to 20 C. and stirring the mixture for two hours, the solution was added into a 10% aqueous solution of hydrochloric acid that had been cooled to 10° C. Then, after the aqueous phase was extracted with benzene and the organic phase was washed with diluted hydrochloric acid and brine, the solvent was removed by distillation under reduced pressure to give 4-bromobutyrophenone in a 84.7% yield from 4-bromobutyryl chloride.

Example 2

In this Example, 0.45 g of the 4-bromobutyrophenone (purity: 94%, 1.86 mmol) obtained in Example 1 was dissolved in 2.2 g of methanol, and 0.14 g of 5% Pd-C (50% wet) was added, followed by stirring the mixture in a hydrogen atmosphere at 20° C. for four hours. The catalyst was filtered off and the solvent was removed by distillation under reduced pressure to give 1-bromo-4-phenylbutane in a 98.2% yield from 4-bromobutyrophenone.

Example 3

In this Example, 14.2 g of 4-bromobutyric acid (85 mmol) was dissolved in 10 g of benzene (128mmol) and, after the temperature was raised to 60° C., 11.9 g of thionyl chloride (100 mmol) was dropwise added. Thereafter, the temperature was raised to 65 to 75° C. and the mixture was stirred at that temperature for one hour. Then, after the mixture was cooled to 20° C., the reaction solution was dropwise added into a suspension solution of 30 g of benzene (256 mmol) and 12 g of aluminum chloride (90 mmol) at 10° C. After stirring the mixture at that temperature for one hour, the temperature was raised to 20° C. and the mixture was further stirred for 30 minutes and added into a 10% aqueous solution of hydrochloric acid that had been cooled to 10° C. Then, the aqueous phase was extracted with benzene, and the organic phase was washed with diluted hydrochloric acid, an aqueous solution of sodium hydrogencarbonate, an aqueous solution of sodium hydroxide, and brine, followed by removing the solvent by distillation under reduced pressure to give 4-bromobutyrophenone in a 62.0% yield from 4-bromobutyric acid.

Example 4

In this Example, 8.35 g of 4-bromobutyric acid (50 mmol) was dissolved in 10 g of benzene (128mmol) and, after the temperature was raised to 60° C., 3.43 g of phosphorus trichloride (24 mmol) was dropwise added. Thereafter, the mixture was stirred at that temperature for one hour. Then, after the mixture was cooled to 20° C., the reaction solution was dropwise added into a suspension solution of 20 g containing benzene (256 mmol) and 6.7 g of aluminum chloride (50 mmol) at 10° C. After stirring the mixture at that temperature for one hour, the temperature was raised to 20° C. and the mixture was further stirred for 30 minutes and added into a 10% aqueous solution of hydrochloric acid that had been cooled to 10° C. Then, the aqueous phase was extracted with benzene, and the organic phase was washed with diluted hydrochloric acid, an aqueous solution of sodium hydrogencarbonate, and brine, followed by removing the solvent by distillation under reduced pressure to give 4-bromobutyrophenone in a 73.9% yield from 4-bromobutyric acid.

Example 5

A mixture solution of 8.6 g of γ-butyrolactone (100 mmol), 34.4 g of 47% aqueous solution of HBr (200 mmol)

and 30 g of benzene was stirred at 55 to 60° C. for one hour. Thereafter, the mixture was further heated and, after about 70 to 80% of water was removed by azeotropy, the mixture was cooled to 20° C. for separation. From the obtained organic phase, benzene was partially removed by distillation under reduced pressure to give 23.7 g of a benzene solution containing 4-bromobutyric acid.

Example 6

Into 23.7 g of the benzene solution of 4-bromobutyric acid obtained in Example 5, was added 4.5 g of phosphorus trichloride (33 mmol) dropwise at 20° C. After the temperature was raised to 60 to 70° C., the mixture was stirred for three hours. Then, after the mixture was cooled to 20° C., the reaction solution was dropwise added into a suspension solution containing 20 g of benzene (256 mmol) and 13.3 g of aluminum chloride (100 mmol) at 10° C. After stirring the mixture at that temperature for 30 minutes, the temperature was raised to 20° C. and the mixture was further stirred for one hour and added into a 10% aqueous solution of hydrochloric acid that had been cooled to 10° C. Then, the aqueous phase was extracted with benzene, and the organic phase was washed with diluted hydrochloric acid and brine, followed by partially removing benzene by distillation under reduced pressure to give 92.1 g of a benzene solution of 4-bromobutyrophenone.

Example 7

Into 92.1 g of the benzene solution obtained in Example 6 and containing 4-bromobutyrophenone was added 1.5 g of 5% Pd-C (50% wet), followed by stirring the mixture in a hydrogen atmosphere at 20° C. for 24 hours. The catalyst was filtered off and benzene was removed by distillation under reduced pressure to give 1-bromo-4-phenylbutane in a 63.9% yield from γ-butyrolactone.

We claim:

1. A process for producing 1-bromo-4-phenylbutane of the formula (1):

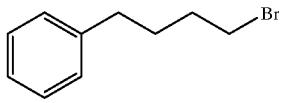

(1)

which comprises the steps of;

reacting 4-bromobutyryl halide of the formula (2):

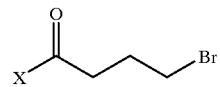

(2)

where X is a halogen atom, with benzene in the presence of a Lewis acid to give 4-bromobutyrophenone of the formula (3):

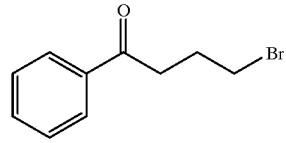

(3)

and reacting 4-bromobutyrophenone of the formula (3) with hydrogen in the presence of a metal catalyst.

2. A process for producing 1-bromo-4-phenylbutane according to claim 1, wherein benzene is used as a solvent in all steps.

3. A process for producing 1-bromo-4-phenylbutane according to claim 1, wherein the metal catalyst is a palladium, platinum, nickel, or ruthenium catalyst.

4. A process for producing 1-bromo-4-phenylbutane according to claim 1, wherein the 4-bromobutyryl halide of the formula (2) is obtained by reacting 4-bromobutyric acid with a halogenating agent.

5. A process for producing 1-bromo-4-phenylbutane according to claim 1, wherein the 4-bromobutyryl halide of the formula (2) is obtained by reacting γ-butyrolactone with hydrogen halide to give 4-bromobutyric acid, and reacting said 4-bromobutyric acid with a halogenating agent.

* * * * *